(12) United States Patent
Henson et al.

(10) Patent No.: US 7,300,661 B2
(45) Date of Patent: Nov. 27, 2007

(54) ADDING MICROSCOPIC POROSITY TO THE SURFACE OF A MICROCOIL TO BE USED FOR MEDICAL IMPLANTATION

(75) Inventors: Michael Henson, Coto De Caza, CA (US); Robert A. Stern, Los Altos, CA (US)

(73) Assignee: Micrus Endovascular Corporation, San Jose, CA (US)

(*) Notice: Subject to any disclaimer, the term of this patent is extended or adjusted under 35 U.S.C. 154(b) by 0 days.

(21) Appl. No.: 11/435,363

(22) Filed: May 16, 2006

(65) Prior Publication Data

US 2006/0251700 A1 Nov. 9, 2006

Related U.S. Application Data

(63) Continuation of application No. 11/340,422, filed on Jan. 26, 2006.

(60) Provisional application No. 60/647,516, filed on Jan. 26, 2005.

(51) Int. Cl.
*A61F 13/00* (2006.01)
*A61M 29/00* (2006.01)

(52) U.S. Cl. .................................... 424/422; 606/200
(58) Field of Classification Search ................ 424/422; 623/1.39; 606/151, 200, 213, 214, 191
See application file for complete search history.

(56) References Cited

U.S. PATENT DOCUMENTS

| 5,449,382 | A  | * | 9/1995  | Dayton ..................... 623/1.15 |
| 6,238,403 | B1 | * | 5/2001  | Greene et al. .............. 606/108 |
| 6,358,556 | B1 | * | 3/2002  | Ding et al. ................ 427/2.24 |
| 6,723,108 | B1 |   | 4/2004  | Jones et al. |
| 2003/0199887 | A1 | * | 10/2003 | Ferrera et al. ............. 606/151 |
| 2004/0193246 | A1 |   | 9/2004  | Ferrera |
| 2004/0210249 | A1 | * | 10/2004 | Fogarty et al. ............ 606/200 |

* cited by examiner

Primary Examiner—Sharon E. Kennedy
(74) Attorney, Agent, or Firm—Fulwider Patton LLP

(57) ABSTRACT

A vasoocclusive microcoil for therapeutic treatment of a patient's vasculature includes a surface with a plurality of voids or pores therein, and a therapeutic or bioactive material disposed within the plurality of voids or pores. The therapeutic or bioactive material within the plurality of voids or pores operates to accelerate a healing process in the patient's vasculature when the microcoil is introduced into the patient's vasculature.

14 Claims, 2 Drawing Sheets

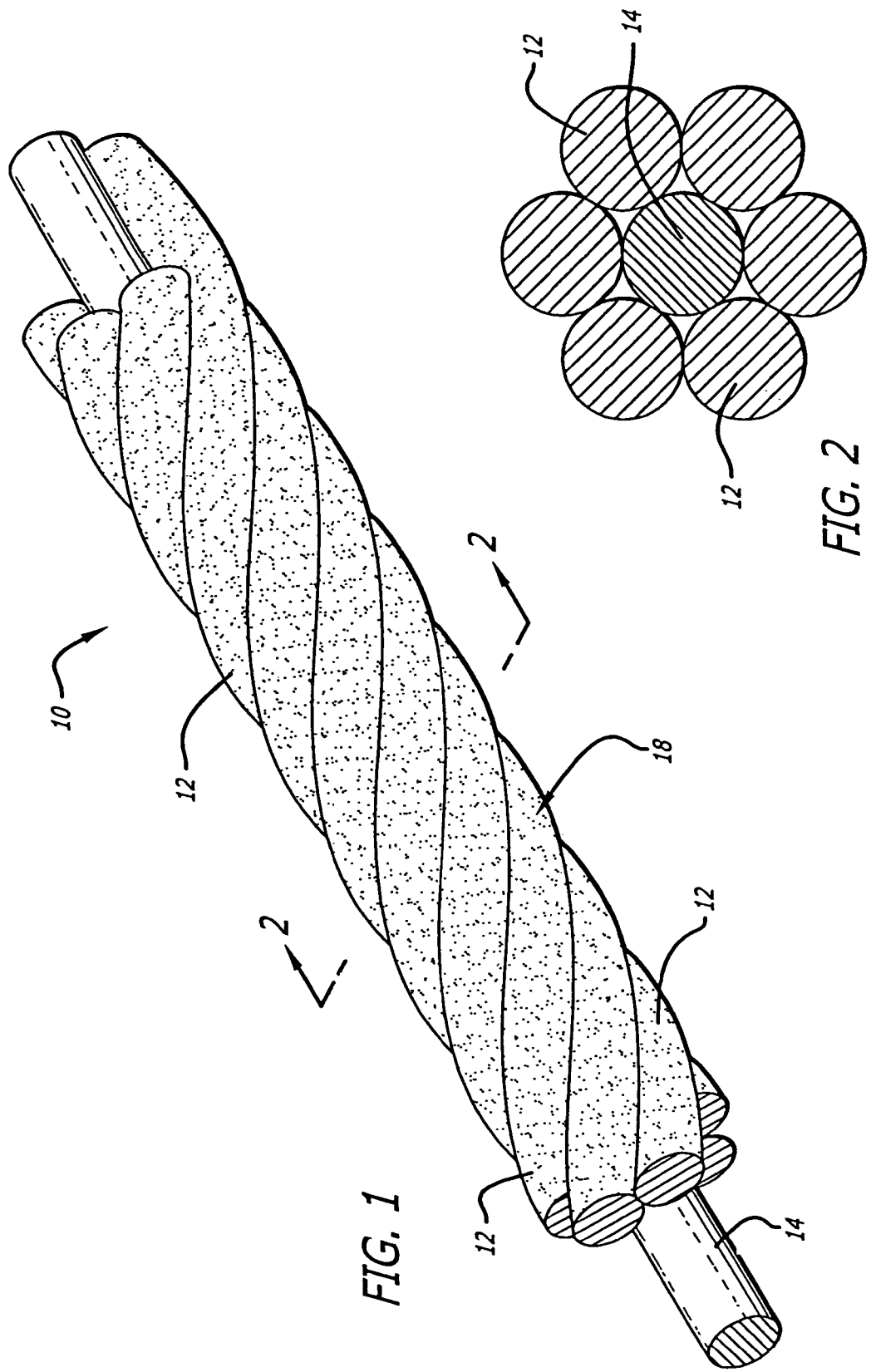

ADDING MICROSCOPIC POROSITY TO THE SURFACE OF A MICROCOIL TO BE USED FOR MEDICAL IMPLANTATION

CROSS-REFERENCES TO RELATED APPLICATIONS

This application is a continuation of Ser. No. 11/340,422, filed Jan. 26, 2006, which is based upon Provisional Patent Application Ser. No. 60/647,516, filed Jan. 26, 2005.

BACKGROUND OF THE INVENTION

Microcoils have been developed for implantability into aneurysms as a means of promoting healing through the obstruction of pulsatile blood flow into the center of the promoting aneurysm. Such devices have become very successful in treatment of cranial aneurysms and as a method of treating and preventing stroke when such malformations are discovered.

Another embolic coil is known which includes a distal roughened, textured surface with pockets having diameters of about 0.125 to 50 microns and depths of about 0.25 to 20 microns to provide improved platelet adhesion and to promote clotting. Another type of removable occlusion system for treating the neck of an aneurysm includes a mesh portion with pores allowing blood to flow through the mesh portion. While such embolic devices have voids or pores that can promote clotting or allow blood flow through the device, it would be desirable to provide an embolic device that can further promote healing of a patient's vasculature.

One vasoocclusive coil is known that has an enhanced therapeutic strand structure that may be formed from or incorporate therapeutic or bioactive materials such as polyglycolic acid (PGA) or poly(D,L-lactic acid-co-glycolic acid) (PGLA), or other therapeutic materials. Another embolic device is known which includes embolizing elements made of a hydrophilic, macroporous, polymeric, hydrogel foam material.

While the microcoil treatment of aneurysms is highly effective in improving the prognosis for recovery of those with such malformations, it is believed that success rate of the procedures would be enhanced if new and effective methods of treatment of the micro coils could be used to enhance the healing process once the microcoils are placed. The present invention resolves these and other limitations in prior art devices.

SUMMARY OF THE INVENTION

The present invention treats microcoils and other implantable devices, using one or more of a variety of etching methods, which can include plasma etching, photolithography and chemical etching, to create microscopic voids in the surface of a microcoil which are complex in shape and adapted to receive into the surface by pressure, melting or deposition one or more of a variety of therapeutic agents, therapeutic materials and therapeutic plastic agents which can act to accelerate the healing process once the coil is in place. At the present time, agents which are believed to be appropriate for deposition in the voids created by the process include therapeutic drugs and agents such as PGA or PGLA, among others, which can act as an accelerant for the healing process.

The present invention accordingly provides for a vasoocclusive microcoil for therapeutic treatment of a patient's vasculature, including a vasoocclusive microcoil having at least a portion having a surface defining a plurality of voids or pores therein, and a therapeutic or bioactive material disposed within the plurality of voids or pores. The present invention also provides for a method for occluding a patient's vasculature, involving the steps of providing a vasoocclusive microcoil having at least a portion having a surface defining a plurality of voids therein, and a therapeutic/bioactive material disposed within the plurality of voids, and introducing the vasoocclusive microcoil into the patient's vasculature, whereby the therapeutic/bioactive material can act to accelerate a healing process in the patient's vasculature. The present invention also provides for a method for delivering a therapeutic agent or material to a patient's vasculature by such a microcoil having at least a portion with a surface having a plurality of voids or pores, and for controlling the delivery of the therapeutic agent or material by controlling the porosity of the surface of the microcoil. The present invention also provides for a method of delivering a hydrogel to a patient's vasculature by a microcoil having at least a portion with a surface having a plurality of voids or pores carrying the hydrogel. The present invention also provides for a method for forming porosity in a surface of a microcoil using one or more of a variety of etching methods, which can include plasma etching and sputtering.

The therapeutic agent or material may be a therapeutic drug or a therapeutic plastic agent which can act to accelerate the healing process once the coil is in place, and in a presently preferred aspect, the therapeutic agent or material may be polyglycolic acid or poly(D,L-lactic acid-co-glycolic acid), and/or a therapeutic drug. More broadly, the therapeutic material may be silk, collagen, elastin, polyglycolic acid, polylactic acid, poly(D,L-lactic acid-co-glycolic acid), poly(L-lactide), poly(L-lactide-co-D,L-lactide), poly(L-lactide-co-glycolide), poly(glycolide-co-trimethylene carbonate), polyethylene oxide, polydioxanone, polycaprolactone, hylauric acid, polyhydroxylbutyrate, poly(phosphazene), poly(D,L-lactide-co-caprolactone), poly(glycolide-co-caprolactone), polyvinyl alcohol, polyanhydrides thereof, poly(ortho esters) thereof, poly(phosphate esters) thereof, poly(amino acids) thereof, poly(hydroxy butyrates) thereof, copolymers thereof, composites thereof, or combinations thereof. The therapeutic material may also be ethylene-octene copolymer, polypropylene, polyethylene, polyacrylate, polyacrylamide, poly(hydroxyethyl methacrylate), polyurethane, polysiloxane, copolymers thereof, composites thereof, or combinations thereof.

Other features and advantages of the present invention will become more apparent from the following detailed description of the preferred embodiments in conjunction with the accompanying drawings, which illustrate, by way of example, the invention.

BRIEF DESCRIPTION OF THE DRAWINGS

FIG. 1 is a perspective of a portion of a microcoil according to the invention.

FIG. 2 is a cross-section at 2-2 of FIG. 1.

DETAILED DESCRIPTION OF THE PREFERRED EMBODIMENTS

Figure 3:
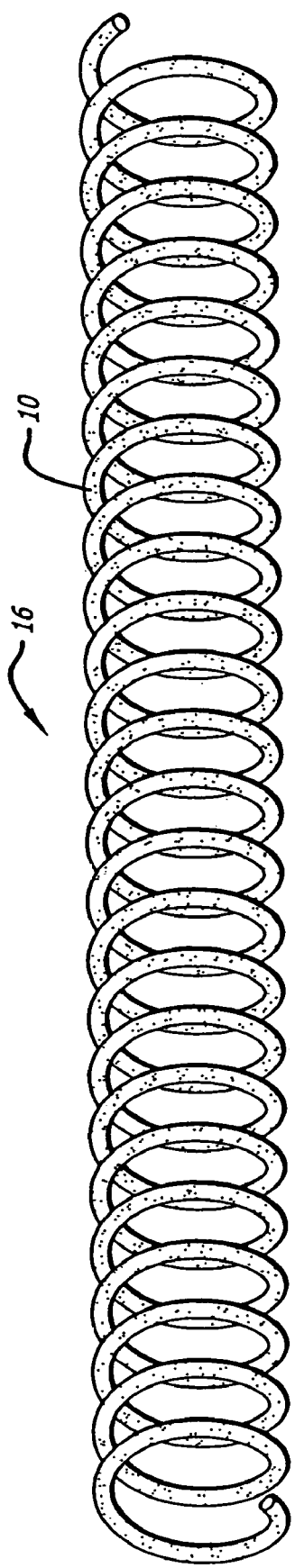
FIG. 3 shows a portion of a helical multi-stranded microcoil formed according to the invention.

As is illustrated in the drawings, which are provided for the purposes of illustration and not by way of limitation, the invention is embodied in a vasoocclusive microcoil having at least a portion with a surface defining a plurality of voids or pores therein, with a therapeutic or bioactive material within the voids or pores. In a presently preferred aspect illustrated in FIG. 1, the vasoocclusive microcoil may be formed from one or more flexible strands 12 of a resilient material and/or super-elastic material, such as nickel titanium alloy, for example. The nickel titanium alloy is typically heat treated such that the alloy is highly flexible at a temperature appropriate for introduction into the body via a catheter. By choosing such a material for micro-coils and the like, the devices formed from the micro-cable can be relatively easily placed into the appropriate body cavity and after placement, the device will take on a shape designed to optimize the therapeutic purposes desired for the device.

As illustrated in FIG. 2, the vasoocclusive microcoil may also include a centrally, axially disposed radiopaque wire 14, which can be formed of platinum or gold, for example, or other similar suitable radiopaque metals, in order to provide a radiopaque marker of the deployed configuration of a device made of the vasoocclusive microcoil during vascular surgery.

Figure 4:
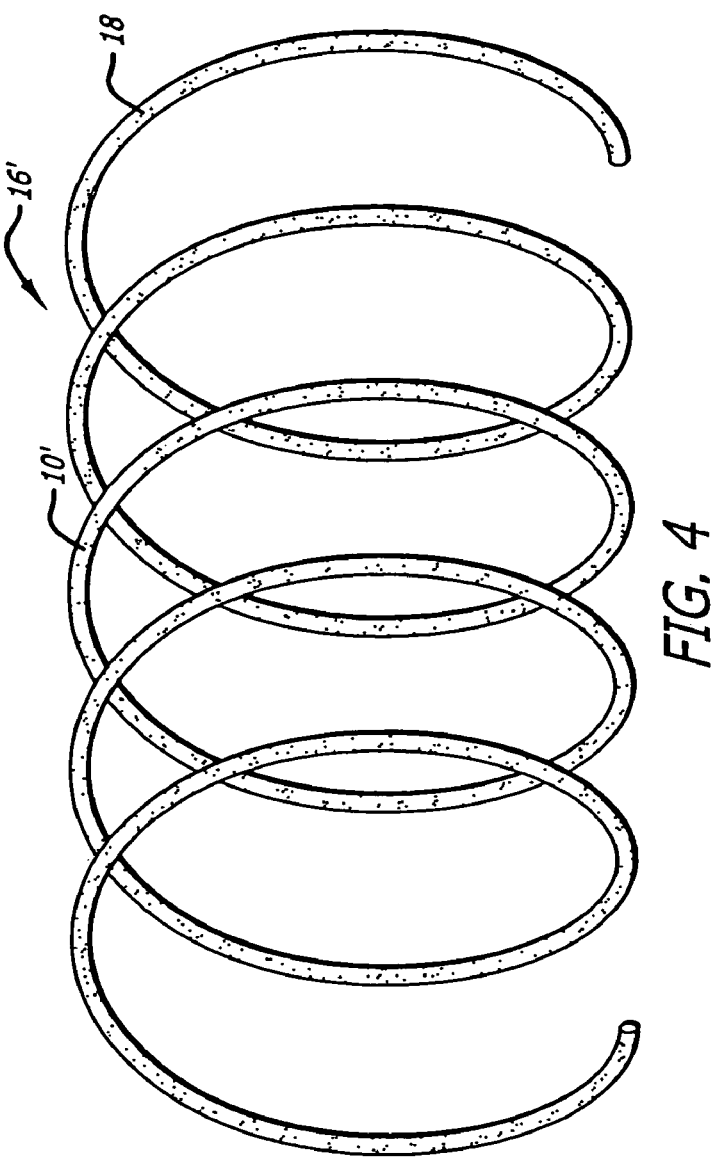
FIG. 4 shows a portion of a helical single-stranded microcoil formed according to the invention.

One advantageous application of the invention is to vasooclusive devices formed of the vasoocclusive microcoil for insertion into aneurysms and other vascular defects for the purpose of occluding flow to the aneurysm. FIG. 3 illustrates a portion of a helically wound coil 16 of the vasoocclusive microcoil 10, which is formed to fit within a micro-catheter for insertion into an area upon which a therapeutic procedure is to be performed. FIG. 4 illustrates a portion of a helically wound coil 16' of the vasoocclusive microcoil 10', which is formed to fit within a micro-catheter for insertion into an area upon which a therapeutic procedure is to be performed. While helical coils are illustrated, it will be appreciated that numerous other shapes can be formed from the vasoocclusive microcoil of the invention.

As is illustrated in FIGS. 1 and 4, the vasoocclusive microcoil includes at least a portion having a surface defining a plurality of microscopic voids or pores 18 in the surface of the microcoil, which may be complex in shape. The voids or pores may be formed in the surface of the microcoil using one or more of a variety of sputtering and etching methods, which can include plasma etching, photolithography and chemical etching, for example, and any combination or combinations thereof. Other methods of creating microscopic voids or pores in the surface of an implantable device can be effective when combined with the ability to deposit, press, or melt a healing accelerant therapeutic and/or bioactive material into the surface.

The voids or pores are advantageously formed to receive and retain a variety of therapeutic and/or bioactive agents which can act to accelerate the healing process once the coil is in place. The agents may be deposited in the voids or pores by pressure, melting or deposition, or the like. At the present time, agents which are believed to be appropriate for deposition in the voids or pores created by the process include polyglycolic acid (PGA) and poly(D,L-lactic acid-co-glycolic acid) (PGLA), which can act as an accelerant for the healing process. Other therapeutic and/or bioactive agents that may be deposited in the voids or pores include polylactic acid or poly(D,L-lactide) (PLA), poly(D,L-lactide-co-glycolide) (PLA/PGA), poly(L-lactide) (PLLA), poly(L-lactide-co-D,L-lactide) (PLLA/PLA), poly(L-lactide-co-glycolide) (PLLA/PGA), poly(glycolide-co-trimethylene carbonate) (PGA/PTMC), polyethylene oxide (PEO), polydioxanone (PDS), polycaprolactone (PCL), hylauric acid, polyhydroxylbutyrate (PHBT), poly(phosphazene), poly(D,L-lactide-co-caprolactone) (PLA/PCL), poly(glycolide-co-caprolactone) (PGA/PCL), polyvinyl alcohol (PVA), polyanhydrides (PAN), poly(ortho esters), poly(phosphate ester), poly(amino acid), poly(hydroxy butyrate), copolymers of these materials as well as composites and combinations thereof; non-metallic fiber material, such as silk, collagen, elastin or other connecting proteins; plastic or other polymers such as an ethylene-octene copolymer, polypropylene, polyethylene, polyacrylate, polyacrylamide, poly(hydroxyethyl methacrylate), polyurethane, polysiloxane and their copolymers. The therapeutic and/or bioactive non-metallic fiber material may be bioabsorbable or non-absorbable. The therapeutic and/or bioactive non-metallic fiber material may also be used for absorbing and releasing one or more therapeutic agents.

It will be apparent from the foregoing that while particular forms of the invention have been illustrated and described, various modifications can be made without departing from the spirit and scope of the invention. Accordingly, it is not intended that the invention be limited, except as by the appended claims.

We claim:

1. A vasooclusive microcoil for therapeutic treatment of a patient's vasculature, comprising:
   a vasooclusive microcoil including at least one flexible metal strand of a resilient material, said at least one flexible metal strand of a resilient material including at least a portion having an exterior surface forming an exterior surface of the vasoocclusive microcoil and defining a plurality of pores having a complex shape therein; and
   a therapeutic/bioactive material disposed within said plurality of pores.

2. The vasoocclusive microcoil of claim 1, wherein said therapeutic material is a plastic agent which can act to accelerate the healing process once the coil is in place.

3. The vasoocclusive microcoil of claim 1, wherein said therapeutic material is selected from the group consisting of polyglycolic acid and poly(D,L-lactic acid-co-glycolic acid).

4. The vasoocclusive microcoil of claim 1, wherein said therapeutic material is selected from the group consisting of silk, collagen, elastin, polyglycolic acid, polylactic acid, poly(D,L-lactic acid-co-glycolic acid), poly(L-lactide), poly(L-lactide-co-D,L-lactide), poly(L-lactide-co-glycolide), poly(glycolide-co-trimethylene carbonate), polyethylene oxide, polydioxanone, polycaprolactone, hylauric acid, polyhydroxylbutyrate, poly(phosphazene), poly(D,L-lactide-co-caprolactone), poly(glycolide-co-caprolactone), polyvinyl alcohol, polyanhydrides thereof, poly(ortho esters) thereof, poly(phosphate esters) thereof, poly(amino acids) thereof, poly(hydroxy butyrates) thereof, copolymers thereof, composites thereof, and combinations thereof.

5. The vasoocclusive microcoil of claim 1, wherein said therapeutic material is selected from the group consisting of ethylene-octene copolymer, polypropylene, polyethylene, polyacrylate, polyacrylamide, poly(hydroxyethyl methacrylate), polyurethane, polysiloxane, copolymers thereof, composites thereof, and combinations thereof.

6. The vasoocclusive microcoil of claim 1, wherein said therapeutic material is a therapeutic drug.

7. A method for occluding a patient's vasculature, comprising:
   providing a vasooclusive microcoil including at least one flexible metal strand of a resilient material, said at least one flexible metal strand of a resilient material including at least a portion having an exterior surface forming an exterior surface of the vasooclusive microcoil and defining a plurality of pores having a complex shape therein, and a therapeutic/bioactive material disposed within said plurality of pores; and introducing said vasoocclusive microcoil into the patient's vasculature, whereby said therapeutic/bioactive material can act to accelerate a healing process in the patient's vasculature.

8. The method of claim 7, wherein said therapeutic material is a plastic agent which can act to accelerate the healing process once the coil is in place.

9. The method of claim 7, wherein said therapeutic material is selected from the group consisting of polyglycolic acid and poly(D,L-lactic acid-co-glycolic acid).

10. The method of claim 7, wherein said therapeutic material is selected from the group consisting of silk, collagen, elastin, polyglycolic acid, polylactic acid, poly(D,L-lactic acid-co-glycolic acid), poly(L-lactide), poly(L-lactide-co-D,L-lactide), poly(L-lactide-co-glycolide), poly(glycolide-co-trimethylene carbonate), polyethylene oxide, polydioxanone, polycaprolactone, hylauric acid, polyhydroxylbutyrate, poly(phosphazene), poly(D,L-lactide-co-caprolactone), poly(glycolide-co-caprolactone), polyvinyl alcohol, polyanhydrides thereof, poly(ortho esters) thereof, poly(phosphate esters) thereof, poly(amino acids) thereof, poly(hydroxy butyrates) thereof, copolymers thereof, composites thereof, and combinations thereof.

11. The method of claim 7, wherein said therapeutic material is selected from the group consisting of ethylene-octene copolymer, polypropylene, polyethylene, polyacrylate, polyacrylamide, poly(hydroxyethyl methacrylate), polyurethane, polysiloxane, copolymers thereof, composites thereof, and combinations thereof.

12. A method for delivering a therapeutic drug to a patient's vasculature, comprising:

providing a vasooclusive microcoil including at least one flexible metal strand of a resilient material, said at least one flexible metal strand of a resilient material including at least a portion having an exterior surface forming an exterior surface of the vasoocclusive microcoil and defining a plurality of pores having a complex shape therein, and a therapeutic drug disposed within said plurality of pores; and introducing said vasoocclusive microcoil into the patient's vasculature.

13. The method of claim 12, further comprising the step of controlling delivery of the therapeutic drug by controlling porosity of said surface defining a plurality of pores therein.

14. A method for delivering a hydrogel to a patient's vasculature, comprising:

providing a vasooclusive microcoil including at least one flexible metal strand of a resilient material, said at least one flexible metal strand of a resilient material including at least a portion having an exterior surface forming an exterior surface of the vasoocclusive microcoil and defining a plurality of pores therein, and a hydrogel disposed within said plurality of pores; and introducing said vasoocclusive microcoil into the patient's vasculature.

* * * * *